US00PP18812P3

(12) United States Plant Patent
Bedford et al.

(10) Patent No.: US PP18,812 P3
(45) Date of Patent: May 13, 2008

(54) APPLE TREE NAMED 'MINNEISKA'

(50) Latin Name: *Malus domestica*
Varietal Denomination: Minneiska

(75) Inventors: David S. Bedford, New Gemany, MN (US); James J. Luby, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 40 days.

(21) Appl. No.: 11/580,467

(22) Filed: Oct. 13, 2006

(65) Prior Publication Data

US 2007/0089206 P1 Apr. 19, 2007

Related U.S. Application Data

(60) Provisional application No. 60/726,438, filed on Oct. 13, 2005.

(51) Int. Cl.
*A01H 5/00* (2006.01)

(52) U.S. Cl. ..... Plt./161

(58) Field of Classification Search ..... Plt./161
See application file for complete search history.

(56) References Cited

U.S. PATENT DOCUMENTS

| | | | | | |
|---|---|---|---|---|---|
| PP2,800 | P | * | 3/1968 | Arends | Plt./161 |
| PP7,197 | P | * | 3/1990 | Luby et al. | Plt./161 |
| PP11,367 | P | * | 4/2000 | Luby et al. | Plt./161 |
| 2007/0089206 | P1 | * | 4/2007 | Bedford et al. | Plt./161 |

* cited by examiner

*Primary Examiner*—Wendy C. Haas
(74) *Attorney, Agent, or Firm*—Penny J. Aguirre

(57) ABSTRACT

A new cultivar of apple tree, 'Minneiska' that is characterized by having fruit with an early ripening season, a crisp and juicy texture and slightly tart but well-balanced flavor. The fruit of 'Minneiska' has an unusually long storage life for an early ripening variety and can be stored for 3 to 4 months with little change in texture or flavor.

3 Drawing Sheets

Botanical classification: *Malus domestica.*
Varietal denomination: 'Minneiska'.

BACKGROUND OF THE INVENTION

The present invention relates to a new and distinct cultivar of apple tree, botanically known as *Malus domestica* 'Minneiska', referred to hereafter by its cultivar name, 'Minneiska'.

'Minneiska' was selected for its unique a combination of fruit traits. Of particular importance is its early ripening season, its very crisp and juicy texture, and its unusually long storage life for an early ripening variety. The crisp and juicy texture is maintained during storage.

'Minneiska' was discovered in 1999 as a seedling tree by the inventors as Tree 46 in Row 23 of Block 86 at Excelsior, Minn. The new apple tree arose from a cross designated AE 8808 made in 1988 between female parent 'Honeycrisp' (U.S. Plant Pat. No. 7,197) and male parent 'Minnewashta' (U.S. Plant Pat. No. 11,367).

Asexual reproduction of the new cultivar was first accomplished by means of budding and grafting by the inventors in Excelsior, Minn. The asexually propagated trees of 'Minneiska' have been determined to be stable and are reproduced true to type in successive generations.

SUMMARY OF THE INVENTION

The following traits have been repeatedly observed and represent the characteristics of the new cultivar. 'Minneiska' has not been observed under all possible environmental conditions. The phenotype may vary somewhat with variations in temperature, day length, light intensity, soil types and water and fertility levels, without, however, any variance in the genotype. The measurements, observations and descriptions that follow describe plants grown outdoors and observed for six years in Excelsior, Minn.

1. 'Minneiska' has an early ripening season with fruit ripening occurring approximately the first week of September in Excelsior, Minn. Ripening time is slightly after 'Minnewashta', and approximately two to three weeks before 'Honeycrisp'.
2. The fruit of 'Minneiska' is about 7.1 to 7.9 cm (2.8 to 3.1 inches) in diameter and conical in shape.
3. The skin fruit color of 'Minneiska' is 70 to 95% red over a yellow-green background.
4. The fruit texture of 'Minneiska' is very crisp, especially for its season of maturity; usually 14 to 19 lbs at harvest.
5. The flavor of the fruit of 'Minneiska' is slightly tart to a well-balanced flavor between sweetness and tartness.
6. The flesh of the fruit of 'Minneiska' is creamy white in color and juicy.
7. The storage life of 'Minneiska' fruit is 90 to 120 days, highly unusual for an early ripening variety.
8. The trees of 'Minneiska' are spreading to slightly upright, are vigorous, and have produced annually under the conditions tested.

'Minneiska' is readily distinguished from its parent 'Honeycrisp' in that the fruit of 'Minneiska' ripen approximately two to three weeks earlier. The tree of 'Minneiska' is more vigorous and more susceptible to apple scab. The fruit of 'Minneiska' are more conic, have more prominent lenticels, and are higher in acidity (0.7% titratable acidity) than fruit of 'Honeycrisp' (0.5% titratable acidity). The fruit of 'Minneiska' have a storage life of 3 to 4 months whereas the fruit of 'Honeycrisp' have a storage life of 7 months. 'Minneiska' is readily distinguished from its parent, 'Minnewashta', in that the flowering time of 'Minneiska' is later (3 to 5 days later at Excelsior, Minn.). The fruit of 'Minneiska' have a storage life of 3 to 4 months whereas the fruit of Minnewashta have a storage life of two months. The fruit of 'Minneiska' are more conic in shape and have greater coverage of red coloration. Fruit of 'Minneiska' seldom drop from the tree prior to harvest whereas 'Minnewashta' trees may show some amount of fruit drop prior to harvest.

The main feature distinguishing 'Minneiska' from other early ripening varieties known to the inventor is the longer time that its fruit can be stored with little change in texture or flavor. 'Minneiska' fruit have a storage life of 3 to 4 months in refrigeration compared to one or two months for other common commercial early season varieties we have observed including 'State Fair' (not patented), 'Arends' (U.S. Plant Pat. No. 2,800), and 'Minnewashta'.

BRIEF DESCRIPTION OF THE DRAWINGS

The accompanying color photographs were taken in Excelsior, Minn. or at an orchard near Lake City, Minn. and illustrate the distinguishing characteristics of the new cultivar 'Minneiska'. The colors in the photographs are as close as possible with the photographic and printing technology utilized. The color values cited in the detailed botanical description accurately describe the colors of the new apple tree.

DETAILED BOTANICAL DESCRIPTION

Figure 1:
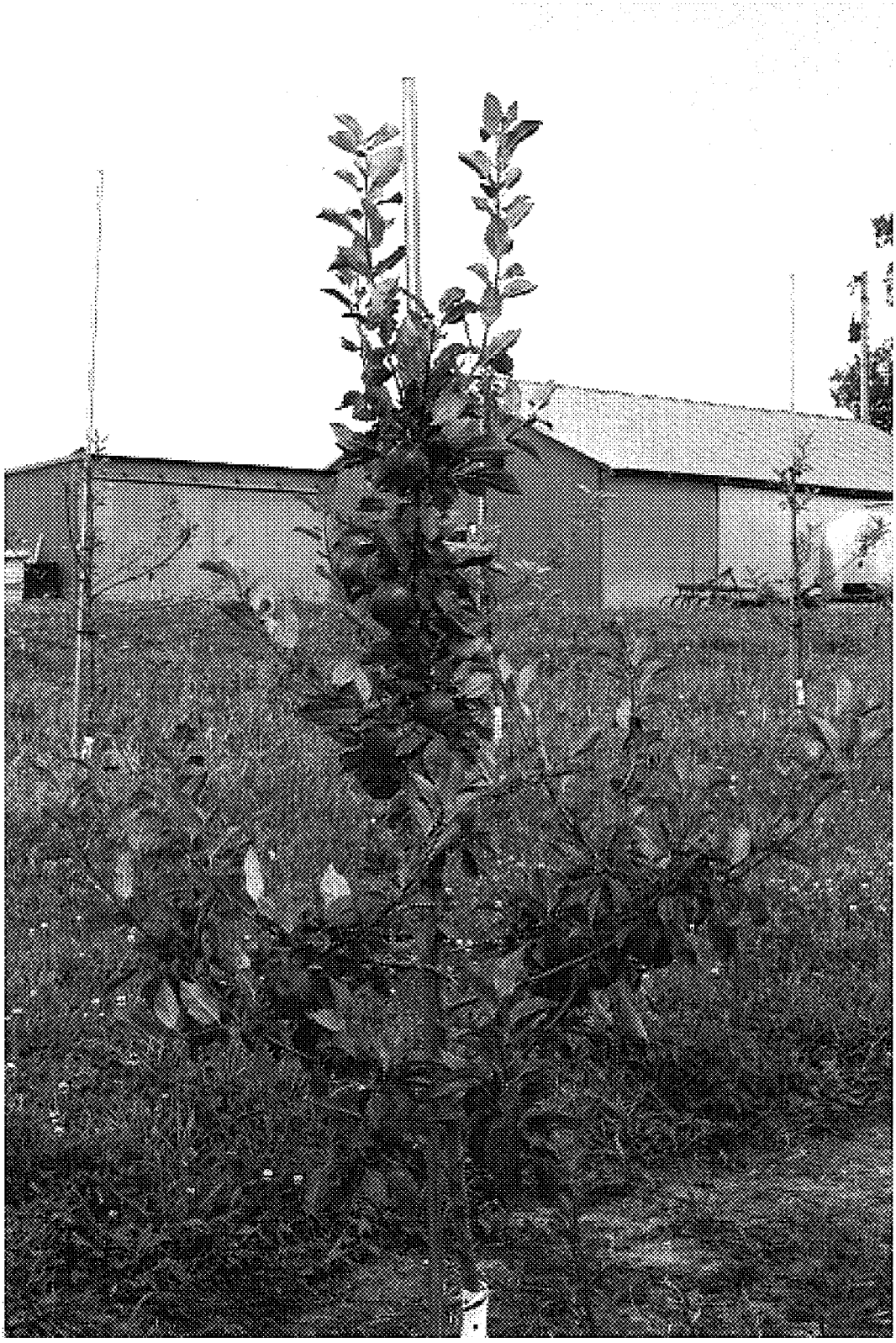
FIG. 1 shows a tree of 'Minneiska' budded onto 'Budagovsky 9' (unpatented) rootstock in its second year in the orchard near Lake City, Minn.
Figure 2:
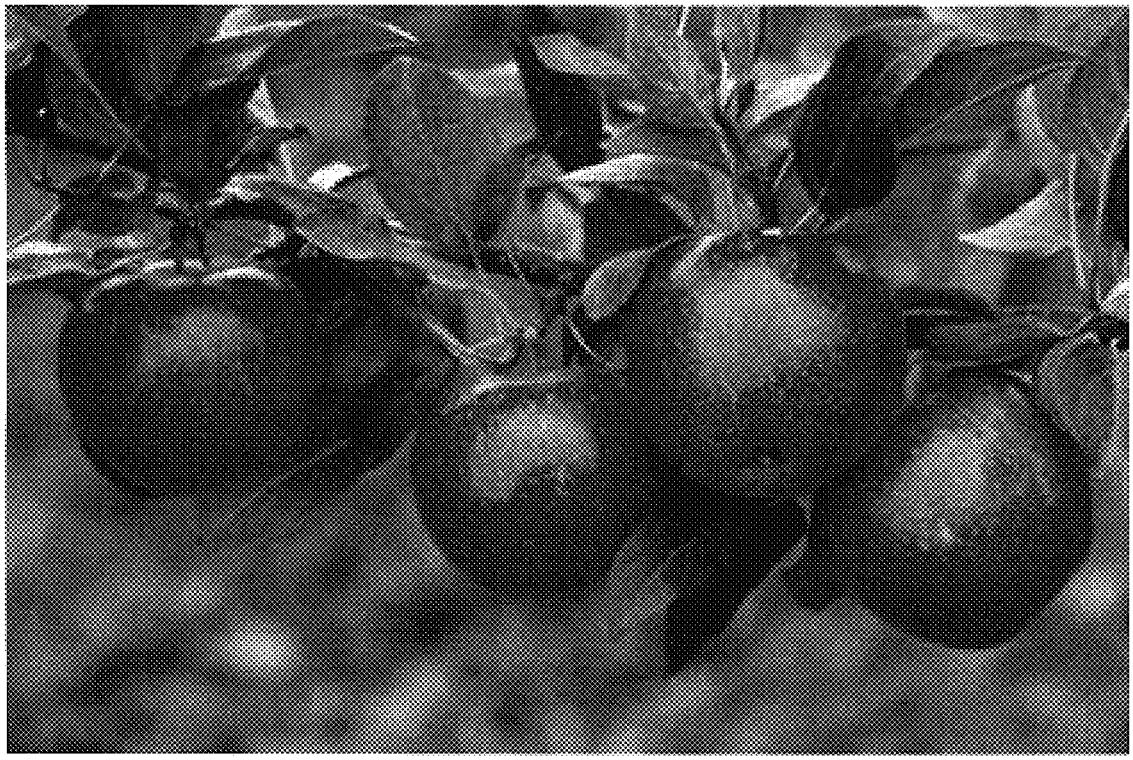
FIG. 2 shows a branch of 'Minneiska' with mature fruit.
Figure 3:
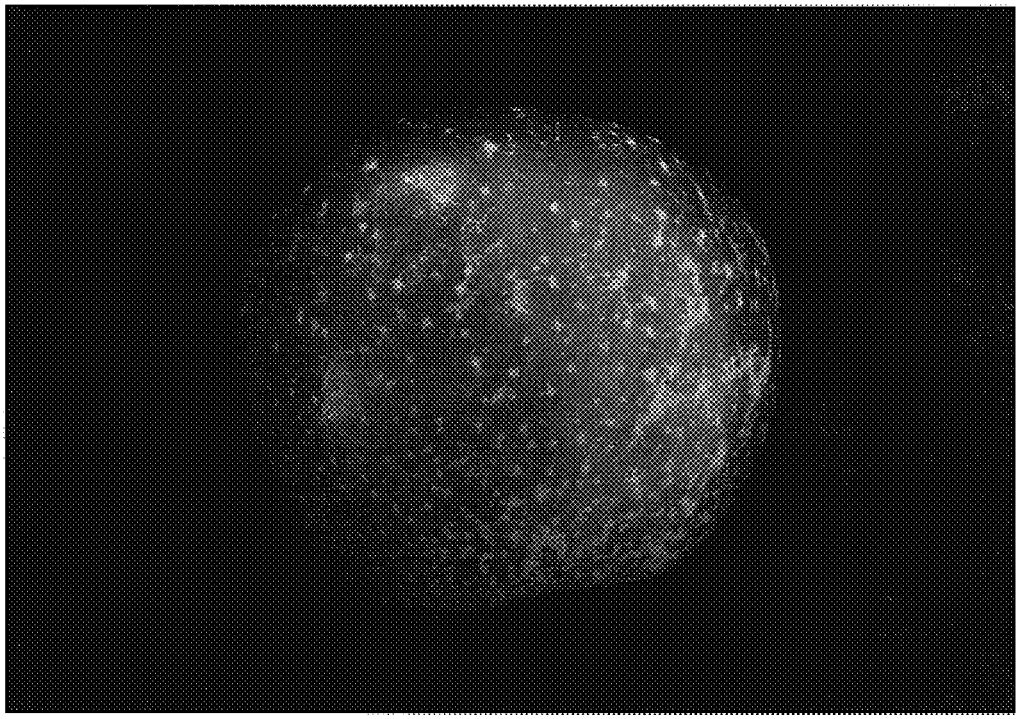
FIG. 3 provides a close-up view of a mature fruit of 'Minneiska'.
Figure 4:
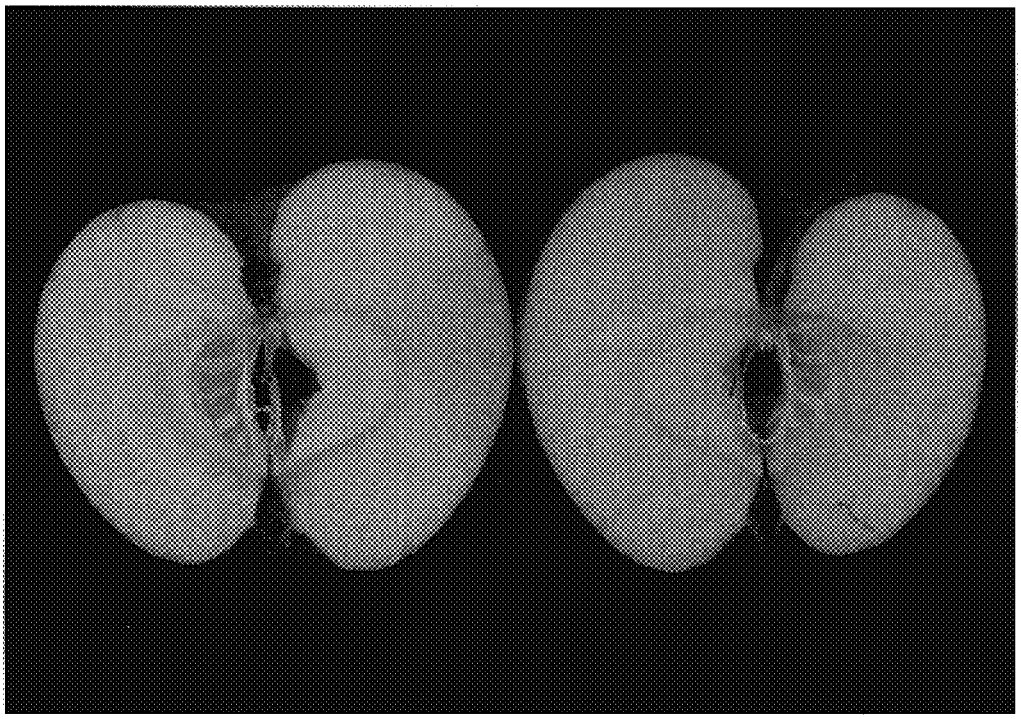
FIG. 4 provides a close-up view of the flesh of a mature fruit of 'Minneiska'.

The following is a detailed description of the new apple variety as observed growing in five field settings for six years in Excelsior, Minn. including the original seedling tree and trees produced by budding or grafting from the original tree. The color names and numbers refer to The 1995 Royal Horticultural Society's Colour Chart, London, England; except for general color terms of ordinary dictionary significance are used.

Botanical classification: Cultivar of *Malus domestica.*
Parentage: 'Honeycrisp' (female), 'Minnewashta' (male).
Tree description:
- *Tree habit.*—Spreading to slightly upright.
- *Vigor.*—Medium high.
- *Diseases resistance.*—Appears to have average susceptibility to apple scab and fire blight.
- *Hardiness.*—U.S.D.A. Zone 4.
- *Branching habit.*—Spreading to slightly upright.
- *Branch frequency.*—Medium.
- *Branch strength.*—Intermediate.
- *Angle of bearing branches.*—Approximately 90°.
- *Predominance of bearing.*—Both spurs and shoots (including tips of shoots).

Description of dormant shoots:
- *Pubescence on upper one year-old shoot.*—Medium.
- *Shine of bark.*—Weak.
- *Thickness of shoot at center of middle internode.*—Means 5.2 mm (range 4.0 to 7.0 mm).
- *Bark color (using bark on 1 year old shoots exposed to sun).*—Reddish brown 183B.
- *Shoot angle.*—Approximately 90°.
- *Lenticel.*—Medium in size and number, color 159C.

Description of growing shoots.
- *Color of growing tip of shoot.*—193A.
- *Shape of shoot tip leaves in cross section.*—Concave.
- *Pubescence.*—Weak to medium on upper side of leaf and dense on lower side.
- *Color of lower side of shoot tip leaves.*—194B on lower side and 146C to 146B on upper side.
- *Distribution of color other than green on shoot tips leaves.*—None.

Leaf description:
- *Leaf orientation.*—Outward.
- *Leaf division.*—Simple.
- *Leaf shape.*—Ovate or oval.
- *Leaf blade size.*—Average of 10.2 cm in length and 5.6 cm in width ($4^{th}$ to $6^{th}$ leaf).
- *Leaf apex.*—Mostly cuspidate.
- *Leaf base.*—Oblique or cuneate.
- *Leaf surface.*—Medium glossiness on upper surface, pubescent on lower surface.
- *Leaf margin.*—Mostly crenate to slightly serrate.
- *Leaf color.*—Upper surface 147A, lower surface 147C.
- *Leaf anthocyanin on lower surface.*—Only at base of petiole 187D.
- *Leaf venation.*—Pinnate main veins with netted minor veins.
- *Petiole size.*—Average of 3.25 cm in length, 1.9 in diameter.
- *Petiole color.*—Green (145B). May have tinge of anthocyanin in the basal 5 mm.
- *Stipules.*—Small to medium in size (mean 11 mm, range 9 to 13 mm), only found on actively growing shoots where they are present on newly developed leaves but abscise on older leaves.

Flower description:
- *Flowering period.*—Mid to late season.
- *Beginning flowering date.*—Typically about May $8^{th}$, after 'Minnewashta' and similar to 'Honeycrisp'.
- *Number of flowers.*—Average of 6 per cluster.
- *Inflorescence type.*—Corymb of rotate flowers.
- *Flower buds.*—68A in color at pink tip stage, round to conical in shape, average of 1 cm in length and 5 cm in diameter.
- *Flower size.*—Average of 5.4 mm in diameter, 1.5 cm in depth.
- *Flower fragrance.*—Mild.
- *Flower aspect.*—Upright.
- *Petals.*—5 per flower, un-fused, mostly overlapping, ovate in shape, obtuse apex, round base, entire margin, about 2.1 cm in length and 1.3 cm in width, color of upper surface is whiter than 155D, color of lower surface is 155D tinged with purple 84B.
- *Sepals.*—5 per flower, 141D in color with tips 78B (upper and lower surface), slight to moderate pubescence, triangular in shape, entire margin, acute apex, fused base, average of 1 cm in length and 3.6 mm in width.

*Pedicel.*—144A in color, average of 1.9 cm in length and 2 mm in width.

*Pistil.*—Compound carpel with 5 stigmas fused at base, 1 cm in length, style is 150B in color and 8 mm in length, stigma is 150B in color, ovary is pubescent and 139D in color.

*Stamens.*—About 19 per flower, anther is oblong in shape, 10A in color and 2 mm in length, pollen is 1C in color and moderate in abundance.

Fruit description:

*Fruit size.*—Medium to large, 7.1 to 7.9 cm in diameter, 6.0 to 7.0 cm in height.

*Position of maximum diameter.*—Midway between proximal and distal ends.

*Fruit shape.*—Globose conical.

*Fruit symmetry.*—Mostly asymmetric due to variation at the distal end.

*Fruit prominence of ribbing.*—Weak.

*Fruit aperture of eye.*—Usually closed.

*Size of eye.*—Medium (mean 9.5 mm, range 6 to 13 mm).

*Persistence of calyx.*—Persistent at harvest.

*Length of sepal.*—Medium (mean 6.3 mm, range 4 to 9 mm).

*Spacing of sepals at base.*—Mostly overlapping.

*Depth of eye basin.*—Medium (mean 5.6 mm, range 4 to 8 mm).

*Width of eye basin.*—Medium (mean 28.4 mm, range 23 to 30 mm).

*Thickness of stalk.*—Medium (mean 2.5 mm, range 2 to 4 mm).

*Length of stalk.*—Short to medium (mean 17.9 mm, range 12 to 25 mm).

*Depth of stalk cavity.*—Medium (mean 14.1 mm, range 12 to 16 mm).

*Width of stalk cavity.*—Medium (mean 33.2 mm, range 28 to 36 mm).

*Relief of surface.*—Smooth except for lightly protruding lenticels or russet areas.

*Bloom of skin.*—Light or medium.

*Waxiness of skin.*—Weak.

*Thickness of skin.*—Medium.

*Skin color.*—Pale yellow (12D) to yellow-green (150B) with red overcolor ranging from 46D in light areas to 46A in dark areas, overcolor amount is 70 to 95% of surface, overcolor type is blushed with faint striping.

*Presence of russet.*—Variable. Always present around stalk cavity. On some fruit it may be more extensive spreading from the stalk cavity through the equatorial region to the eye basin, ranging from small streaks to an extensive netted pattern.

*Lenticels.*—Medium to large (mean 1.1 mm, range 0.7 to 1.7 mm), intermediate to high prominence.

*Color of flesh.*—Creamy white (158A).

*Distinctness of core line.*—Very weak.

*Aperture of locules.*—Closed.

*Fruit set.*—Intermediate.

*Fruit maturity date.*—Early, harvest season is approximately the first week of September in east central Minnesota, slightly after 'Minnewashta' and approximately two to three weeks before 'Honeycrisp'.

*Seed.*—Brown-grey (199B) when dry, ovoid to somewhat deltoid in shape, length 9.5 mm (range 9.0 to 10.0 mm) and maximum diameter 4.7 mm (range 4.0 to 5.2 mm).

*Browning of flesh.*—Medium.

*Firmness* (*without skin*).—Medium to High, 16 to 19 lbs.

*Texture of flesh.*—Coarse, crisp, and juicy, maintained during storage for 90-120 days.

*Cropping frequency.*—Annually.

*Acidity.*—0.7033% titratable acidity (malic acid equivalent) ('Honeycrisp' 0.5042% titratable acidity).

*Brix.*—14.8° ('Honeycrisp' 14.7°).

*Storage life.*—90 to 120 days in common stage (34 to 37° F.), unusually long storage life for an early ripening variety.

We claim:

1. A new and distinct variety of Apple Tree designated 'Minneiska' as described and illustrated herein.

* * * * *